Figure 1:
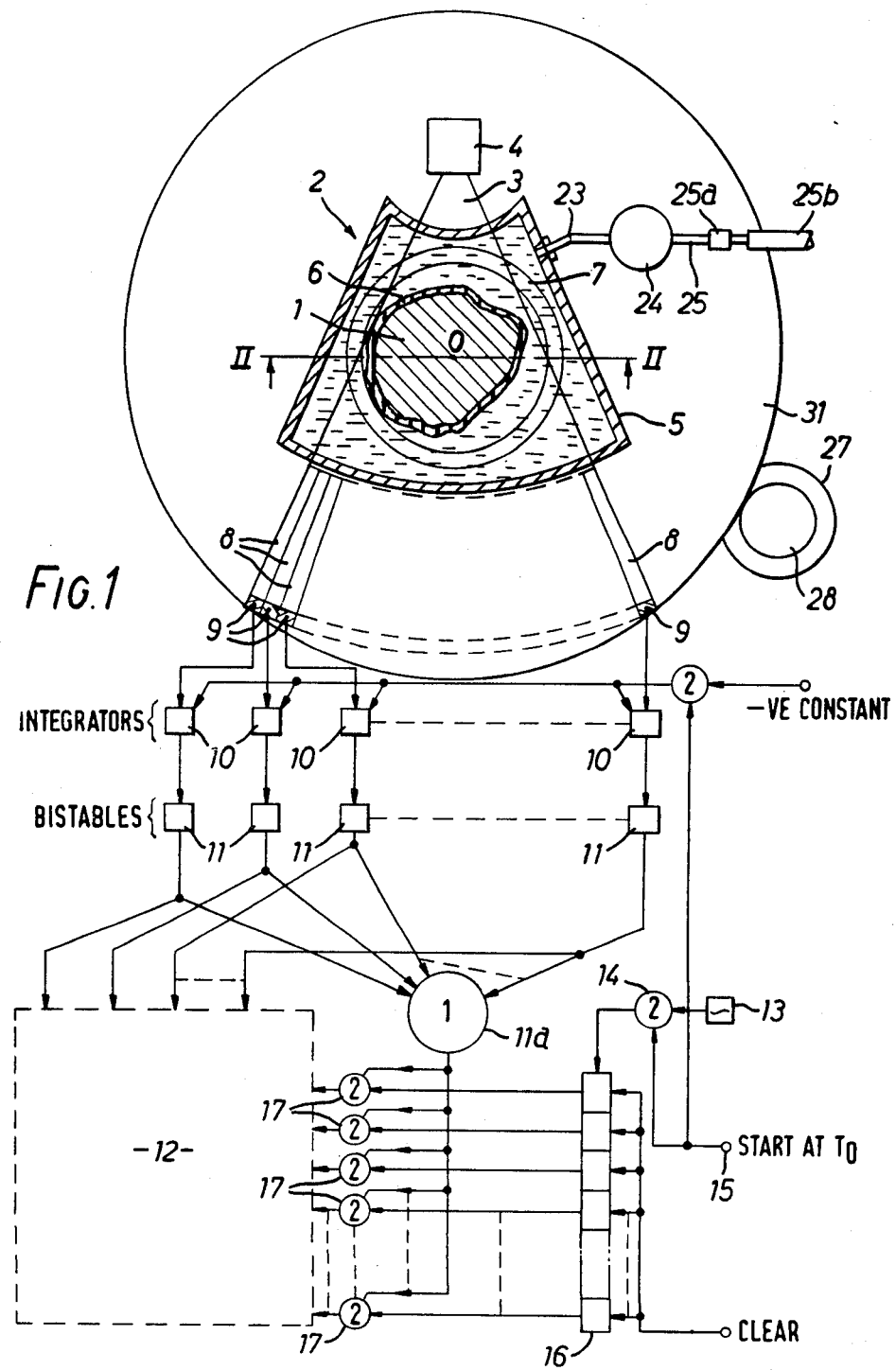

United States Patent [19]

Hounsfield

[11] 4,041,315

[45] Aug. 9, 1977

[54] COMPUTERIZED TOMOGRAPHY COMPRISING LATERALLY SHIFTING DETECTED BEAMS WITHIN A ROTATED FAN OF RADIATION

[75] Inventor: Godfrey Newbold Hounsfield, Newark, England

[73] Assignee: E M I Limited, Hayes, England

[21] Appl. No.: 650,281

[22] Filed: Jan. 19, 1976

Related U.S. Application Data

[60] Continuation of Ser. No. 489,084, July 17, 1974, Pat. No. 3,934,142, and Ser. No. 481,443, June 20, 1974, which is a division of Ser. No. 358,980, May 10, 1973, Pat. No. 3,881,110.

[30] Foreign Application Priority Data

May 17, 1972 United Kingdom ............... 23064/72
July 21, 1973 United Kingdom ............... 34859/73

[51] Int. Cl.² .................. A61B 6/02; G01N 23/08; H05G 1/30
[52] U.S. Cl. ........................... 250/360; 250/369; 250/445 T
[58] Field of Search ............ 250/445 T, 360, 369

[56] References Cited

U.S. PATENT DOCUMENTS 3,973,128  8/1976  Lemay .................... 250/445 T

*Primary Examiner*—Alfred E. Smith
*Assistant Examiner*—T. N. Grigsby
*Attorney, Agent, or Firm*—Fleit & Jacobson

[57] ABSTRACT

A method of radiographically examining a body is disclosed, wherein a spread of penetrating radiation is projected through a cross-sectional region of the body from a plurality of locations distributed angularly around the body, thus permitting the derivation of signals indicative of the absorption suffered by the radiation on traversing said region along each of a number of mutually divergent beam paths within said spread, for each of said locations. The positions of the beam paths within the spread for irradiation of the body from some of said locations differ from the positions of said paths within said spread for irradiation of the body from others of said locations so as to permit the derivation of signals relating to interleaving beam paths through said region.

1 Claim, 8 Drawing Figures

COMPUTERIZED TOMOGRAPHY COMPRISING LATERALLY SHIFTING DETECTED BEAMS WITHIN A ROTATED FAN OF RADIATION

This application is related to and continuing from U.S. patent application Ser. No. 481,443, filed June 20, 1974, which is a divisional application from application Ser. No. 358,980 filed May 10, 1973, now U.S. Pat. No. 3,881,110. This application is also related to and continuing from U.S. patent application Ser. No. 489,084, filed July 17, 1974 now U.S. Pat. No. 3,934,142.

The present invention relates to radiography, and it relates in particular to apparatus for examining a thin planar slice or section of a body.

In our British Patent Specification No. 1,283,915 there is described apparatus for examining a thin planar slice of the human body. In one form of the apparatus a source of X-radiation produces a collimated beam which is directed through the body to a detector disposed at the other side of the body from the source. scanning movements are imparted to the source and detector which are such that the beam executes successive traverses at right angles to its length, so that the beam sweeps through the slice under examination. After each such traverse, the source and detector are rotated through a small angle, say, 1°, so that the successive traverse occurs with the beam in different angular dispositions. The output of the detector is sampled during each traverse so that successive output signals are obtained dependent on the transmissions of the beam through a succession of narrow paths which during any one traverse are parallel to one another. The sampling is carried out so that the signals derived during any one traverse are dependent on the transmission or absorption of all elements of the body in the planar slice swept by the beam during the particular traverse. From the many sets of output signals thus obtained, corresponding to sets of parallel beam paths, disposed at different angular orientations, a reconstruction of the absorption or transmission of the elements in the planar slice is produced. The scanning procedure outlined above is however relatively slow, and for the examination of parts of the body which move due to heart beats or breathing, a faster scanning technique is required. With a view to providing such a technique it has been proposed to irradiate the entire slice under examination with a swath of radiation and to detect the transmission along narrow beams in the swath by means of a bank of collimated detectors, each detector thus providing the output of a single beam. With such an arrangement, the lateral scanning traverses can be dispensed with and the scanning can be effected by a continuation orbital movement of the source and the detectors. However, the need to provide a bank of detectors with associated collimators has the disadvantage that gaps are left between the adjacent beams. This means either that each set of output signals may include fewer than the desired number, or that narrower beams have to be used, reducing the signal to noise ratio of the signals.

The object of the present invention is to reduce this disadvantage.

Figure 2:
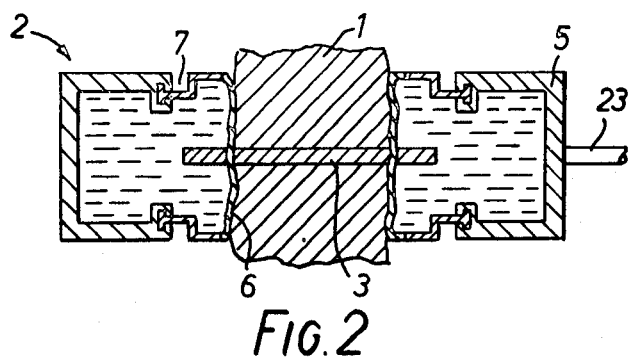
Figure 4A:
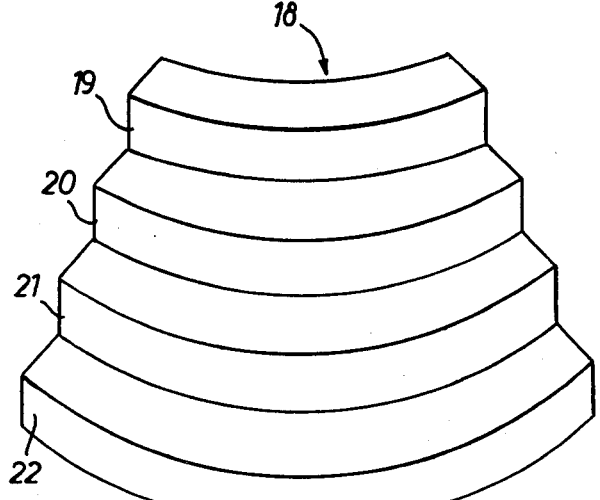
Figure 3:
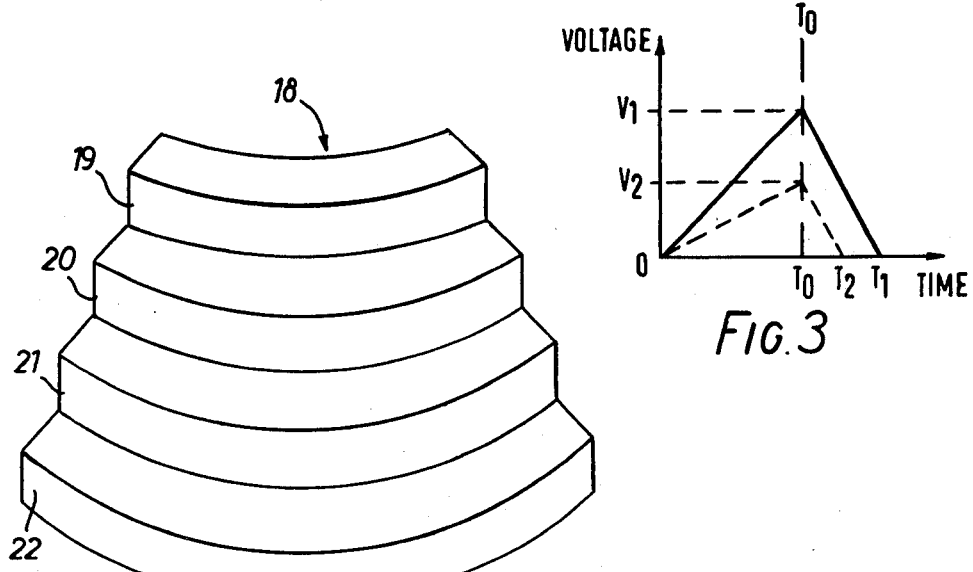
Figure 5:
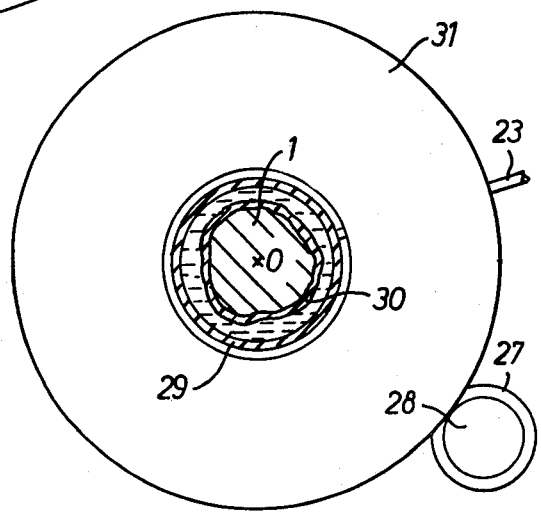
Figure 4B:
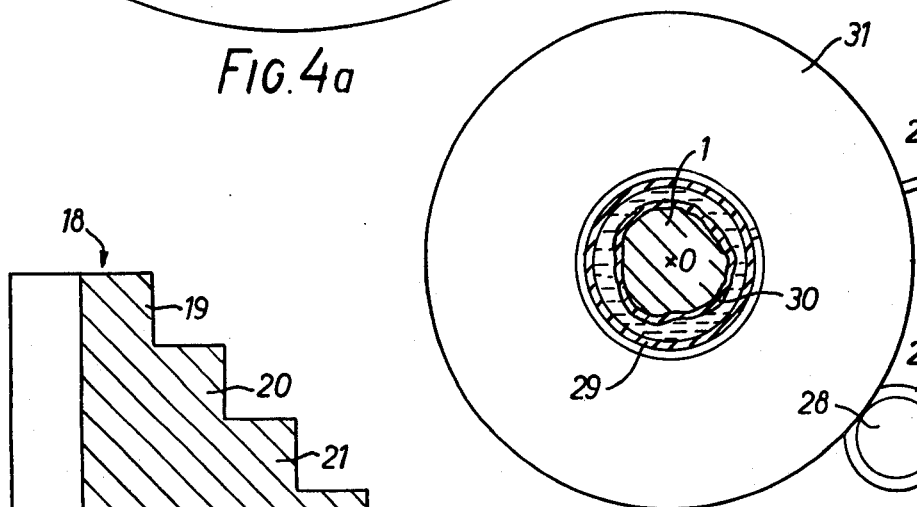
Figure 6:
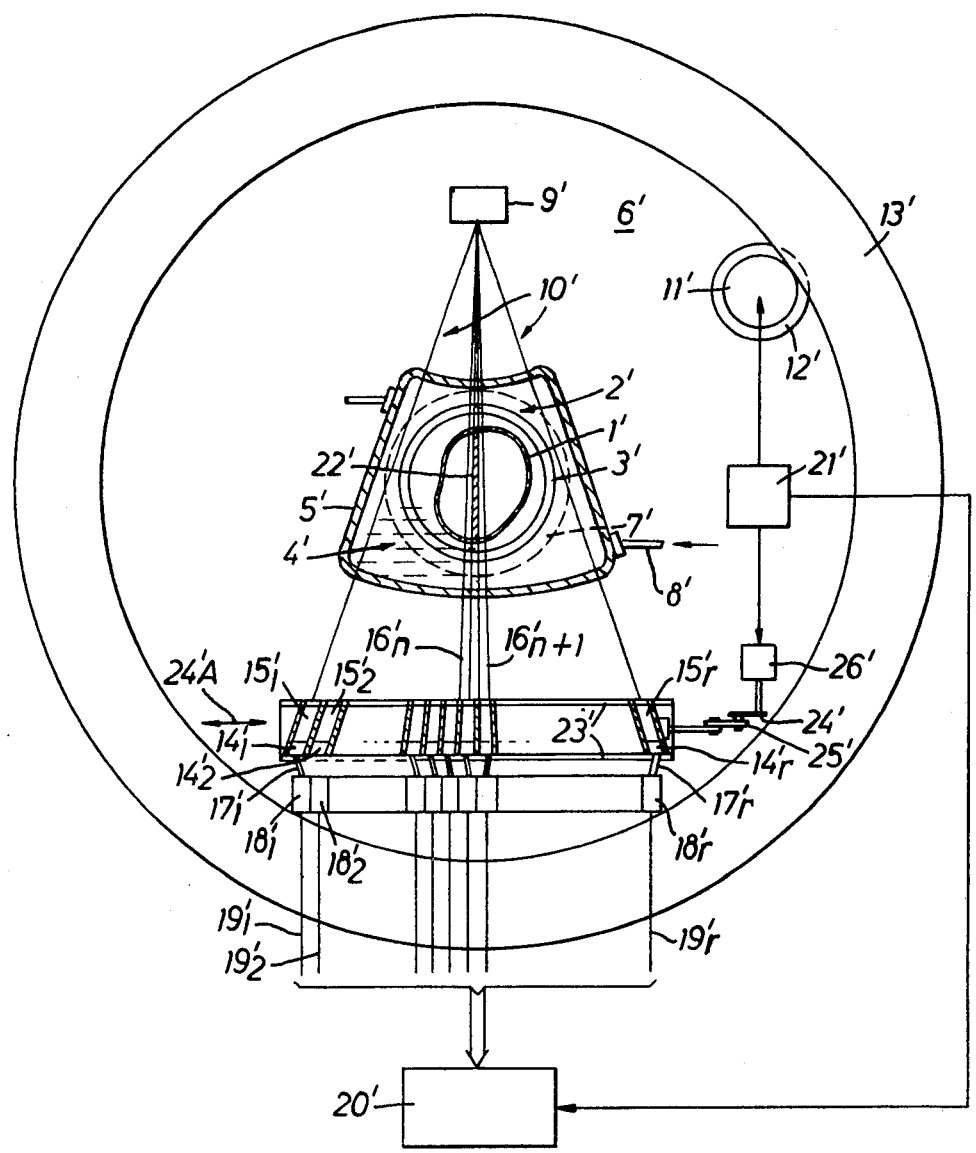
Figure 7:
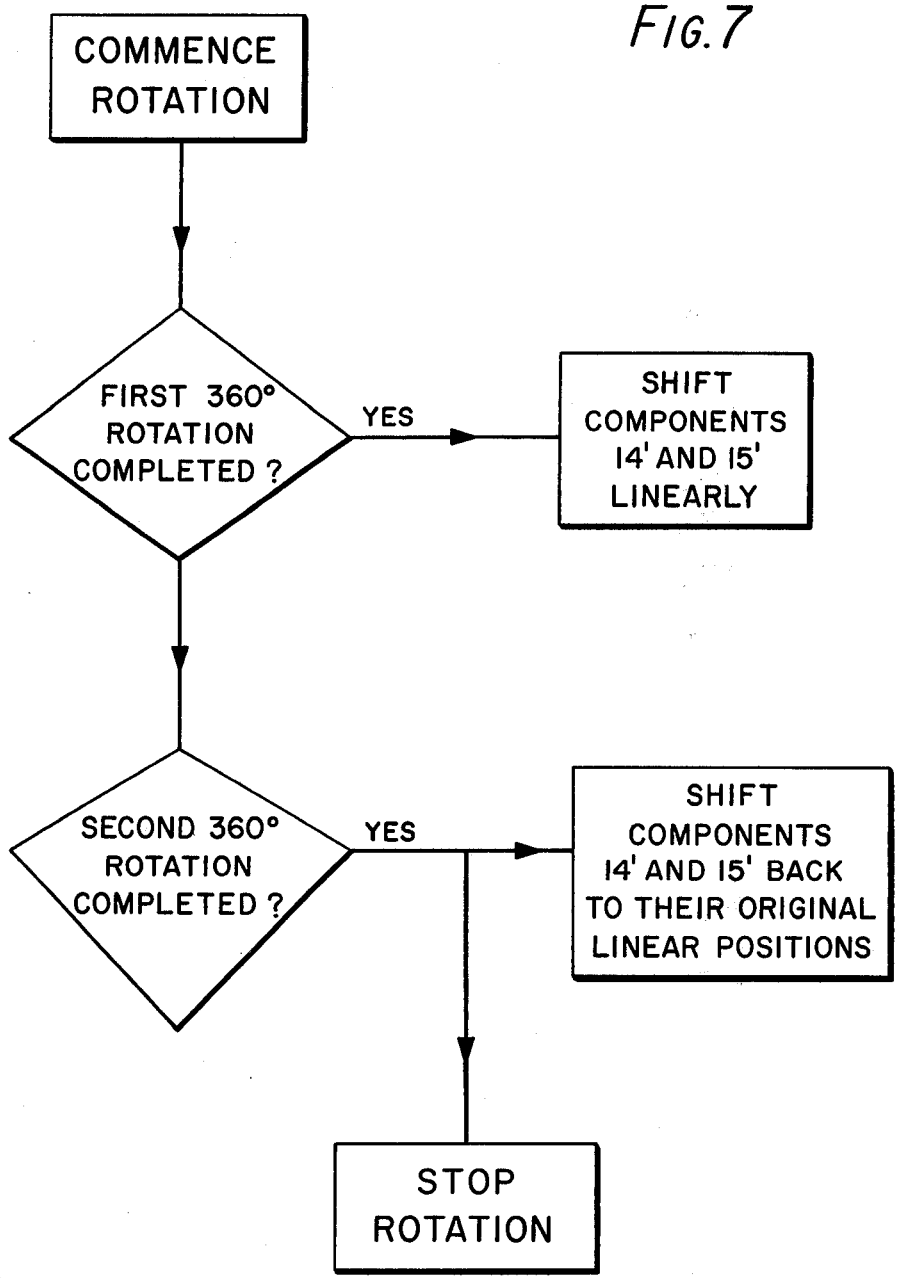

In order that the invention may be clearly understood and readily carried into effect, the same will now be described, by way of example only, with reference to the accompanying drawings, of which:

FIG. 1 illustrates, partly in a plan section and partly in block schematic form, apparatus in accordance with one example of the invention, FIG. 2 shows a section on lines II—II of FIG. 1, FIG. 3 illustrates waveforms explanatory of the operation of the apparatus shown in FIG. 1, FIGS. 4(a) and 4(b) show, in perspective view and cross-sectinal form respectively, a calibration device suitable for use with the apparatus shown in FIG. 1, FIG. 5 shows an alternative form of the invention, FIG. 6 shows, in schematic view, one example of apparatus in accordance with the present invention.

and FIG. 7 shows a four-step flow diagram which is explanatory of one embodiment of the invention.

Referring now to the drawings, and more particularly to FIGS. 1 and 2, a body 1 to be investigated is mounted in an arrangement shown generally at 2 so that it can be illuminated by a fan-shaped swath 3 of penetrative radiation, such as X- or γ-radiation, derived from a source 4.

The arrangement 2, in this example, comprises an enclosure of which the outer walls 5 are formed of the material known by the Registered Trade Mark "Perspex" or another suitable material. The arrangement is provided with a central aperture in which the body 1 is situated, the aperture being surrounded by a tubular, flexible wall 6 formed, for example, of rubber. The enclosure between the walls 5, 6 is filled with water as indicated by the horizontal shading lines. Water can be pumped into or out of said enclosure by means of a pump 24 which is reversible in its operation and which communicates with said enclosure by means of a pipe 23 and with a water reservoir (not shown) via a pipe 25, a closure valve 25a and a removeable pipe 25b. Water is pumped out of said enclosure to allow the tubular wall 6 to expand outwardly so that the body 1 can be inserted therein and then water is pumped into said enclosure to cause the wall 6 to fit snugly around the part of body 1 which is to be investigated. In order that the body 1 and the flexible wall 6 may remain stationary whilst the remainder of the enclosure is rotated, a rotary water seal 7 is provided in the arrangement 2. The fan shaped sweep 3 passes through the arrangement 2 as shown in FIG. 2 and it will be appreciated that the snug fit between the flexible wall 6 and the body 1 must be maintained at least over the area through which the beam passes.

Having passed through the body 1, the fan shaped sweep 3 is incident upon a plurality of radially extending collimators 8 and the field of view of each collimator defines a respective, discrete path of radiation through the body 1. In one example, 160 such collimators are used. In order that the overall degree of absorption of radiation along each discrete path can be monitored, each collimator 8 communicates with a respective radiation detector 9 which may take one of several forms to be described hereinafter.

Latch detector 9 feeds a respective integrator circuit 10 and the arrangement is such that (referring to FIG. 3) each integrator receives signals from its respective radiation detector for a given exposure period $T_o$. At time $T_o$, a negative voltage is applied in parallel to all the integrators 10 causing them each to discharge towards zero potential. The time taken for the charge held in a given integrator to reach zero potential will clearly be determined by the amount of charge accumulated up to $T_o$, thus if, for example a first detector accumulated charge corresponding to a potential $V_1$ and a second detector accumulated a lesser amount of charge corresponding to a potential $V_2$, the integrator associated with the first detector would reach zero potential in time $(T_1-T_o)$ whereas the integrator associated with the second detector would reach zero potential in the lesser time $(T_2-T_o)$. Accordingly, referring again to FIG. 1, each integrator 10 is arranged to feed a respective bistable circuit 11 which is such that it provides an output pulse when the input signal thereto reaches zero potential from a more positive potential. The output pulses from all the circuits 11 pass on the one hand through a common OR gate 11a, and on the other hand as path identity signals to a store 12 associated with a computer (not shown).

An oscillator 13 is arranged to generate regularly occurring pulses at a rapid rate and these are applied to an ANd gate 14. The gate 14 is enabled at time $T_o$ by the same control signal as was used to apply the negative potential to the integrator 10, the control signal being applied to a terminal 15, and is arranged to pass the pulses generated by oscillator 13 to a counter 16 continuously from the time $T_o$ to the time when the last of the integrators indicates zero potential.

The counter 16 is a multistage binary counter having sufficient capacity for counting the number of pulses which would be generated by oscillator 13 during the period from $T_o$ to the maximum possible time taken for one of the integrators 10 to indicate zero potential i.e., in the case of zero absorption of the radiation along a given path.

Each stage of counter 16 is connected, via a respective AND gate 17, as a decay time input to the store 12 and the gates 17 are all simultaneously enabled when a pulse derived from any one (or more) of the bistable circuits 11 passes through the OR gate 11a. The store 12 thus receives both path identity and decay time information and the computer is arranged to correlate this information to provide a figure representing the absorption (or transmission) of said radiation along each path. Those figures are then converted into logarithmic values and processed, for example in the manner described in the aforementioned Patent Specification, to provide a representation or a visual record or display of the absorption (or transmission) coefficients of substantially all the elements in a two-dimensional notional matrix of elements defined in the body 1.

In this example, the fan shaped swath is substantially planar, but it could alernatively be caused to have a greater thickness dimension so as to permit a three dimensional notional matrix of elements defined in the body 1 to be investigated.

In operation, the source 4, the part of arrangement 2 outside the water seal 7, together with the pump 24, pipes 23 and 25 and the valve 25a, from which pipe 25b is then detached, the collimators 8 and the detectors 9 are then orbited, about the centre O of the arrangement 2, relative to the body 1 in order to expose the body 1 to radiation from a plurality of different directions. For this purpose the aforementioned components are mounted on a turntable 26 which has an aperture therein corresponding to the diameter of the water seal 7, the turntable being driven by means of an electric motor 27 via a suitable drive mechanism 28 which may comprise, for example, a toothed gear wheel adapted to co-operate with gear teeth provided around the periphery of the turntable 16. It is preferable in some circumstances, especially when the human torso is examined, that the aforementioned components be rotated at a rapid rate in order that the irradiation of the torso can be completed sufficiently rapidly that the time available for movement of internal organs of the body (which movement could cause degradation of the resolution of the apparatus) is limited. In these circumstances, it is preferable for the aforementioned components to be rotated continuously rather than step-wise (as described in the aforementioned Patent Specification). Because of this continuous rotation, each exposure time effectively corresponds to the time taken for the aforementioned components to rotate through a small angle, and in order to reduce or avoid confusion of detail produced by the relative movement between the source and detectors and the body, the computer can be programmed to take account of this.

To evaluate zero for each detector 9 during operation of the apparatus, a shutter (not shown) may be provided between the source 4 and the arrangement 2. This shutter is rotated so that it intermittently interrupts the radiation during each exposure time and the zero reading obtained when the beam of radiation is interrupted is subtracted from the calculated absorption (or transmission) coefficient. The shutter drive mechanism must be synchronised with the mechanism for rotating the aforementioned components of the apparatus so as to enable a zero to be evaluated during each exposure time.

It is possible, as previously mentioned, to utilise one of several arrangements as the detectors 9 and these arrangements are set out below.

EXAMPLE 1

Silicon photodetectors together with an associated wavelength converter phosphor, such as a CsI crystal, for converting the penetrative radiation into optical radiation. The silicon photodetectors can take the form, for example, of p-n junction photodiodes, p-i-n silicon photodiodes, silicon avalanche photodiodes, silicon photofets, silicon planar junction phototransistors or silicon photo-integrated circuits, a respective detector being provided for each collimator.

A problem which arises with photodetectors of this kind is dark current and the detectors require cooling to reduce this phenomenon. If however, the temperature of the array of detectors is stabilised, a higher dark current can be tolerated since it is consistent and can be allowed for by suitably programming the computer.

EXAMPLE 2

Photoemissive diodes together with a wavelength converter phosphor. The diode could comprise, for example, respective separate photodiodes for each collimator; a similar number of diodes in a common vacuum enclosure; channel multiplier diodes; small photomultipliers or gas-filled photomultiplier photocells.

There are practical limitations on attainable sizes of photoemissive diodes, but this disadvantage can be alleviated to some extent by utilising reflecting optical systems.

EXAMPLE 3

An X- (or γ-) ray sensitive vidicon. Grazing incidence reflecting optical elements made from such metals as electroless plated titanium or aluminium have made it possible to obtain good quality X-ray images without using pinhole optics. A difficulty arises however in that an image demagnefication of about 30:1 is required.

EXAMPLE 4

A fibre-optic vidicon fed by respective fibre optic light guides from respective wavelength converter phosphors for each collimator.

EXAMPLE 5

A Digicon tube and a wavelength converter phosphor. The Digicon is a vacuum table containing a semi-transparent photoemissive cathode of the inside of the end window, a series of accelerating and focusing electrodes and a linear array of silicon p-n junction diodes on the window at the other end. A solenoidal focus field is used to direct and focus electrons emitted from the photocathode. The diodes are reverse biassed and, when struck by electrons, the phenomenon of electron bombardment induced conductivity causes them to conduct. The conduction current is about $2 \times 10^3$ or $3 \times 10^3$ times greater than the bombarding current and thus the tube is capable of detecting single photoelectrons. For this application, the Digicon requires a fibre optic end window communicating with the photocathode and fibre optic coupling between the Digicon and respective wavelength converter crystals for each collimator.

EXAMPLE 6

Photographic film. A full size medical X-ray plate is moved mechanically beneath the body in a direction perpendicular to the plane of the fan-shaped beam 3. Thus a series of lines corresponding to the transmitted radiation would be unprinted as a number of dots at each exposure angle. After developing the lines are scanned with a microdensitometer.

In any of the above examples, it can be advantageous, in order to avoid dead spaces between adjacent detectors, to construct the collimators so that adjacent paths overlap to some extent. Alternatively, however, the gaps may be covered by arranging that, in a full 360° sweep around the body, the paths not scanned on one half revolution are scanned during the next half revolution.

It is desirable, in any of the foregoing arrangements, that the individual components of the detecting means should initially be calibrated and then re-calibrated before each new body is examined thereby. To this end, a suitable arrangement has been found to be as follows.

One of the individual components (such as for example the extreme left hand collimator 8 and detector 9 shown in FIG. 1) is calibrated comprehensively by insertion of a wedge of continuously variable thickness (and hence absorbing power) between the source 4 and the collimator 8, and the output signals fed from counter 16 to the computer are noted. Thus the computer is provided with a characteristic response curve for the detecting means. Of course the wedge could be inserted between the source 4 and all the detecting means to enable an average characteristic response curve to be calculated, if desired. Once having provided the computer with a characteristic response curve, it is only necessary, during re-calibration, to provide relatively crude information to the computer, for example an indication of the responses of the detecting means to minimum and maximum amounts of radiation would be sufficient. However in this example the responses of the detecting means under two intermediate conditions, as well as under the two extreme conditions are measured. A sectoral shaped calibration member 18, made up of four layers as shown in FIG. 4(a) and 4(b) is used, the thinnest layer 19 being adapted to transmit substantially all radiation incident thereon, the next thicker layer 20 being adapted to absorb the radiation to some extent, the layer 21 being adapted to absorb the radiation to a greater extent and the thickest layer 22 being adapted to absorb substantially all the radiation incident thereon. In addition to, or instead of being of different thicknesses the layers may be of different materials. In operation, the calibration member 18 is lowered step-wise into the path of the fan-shaped swath 3, so that the amount of radiation passed through each layer of member 18 is monitored by each detecting means and the output signals derived from the detecting means are processed as described with reference to FIG. 1, the process terminating in a rough re-calibration curve for each component of the detecting means being applied to the computer for comparison with the stored characteristic response curve. After the comparison has been effected, the computer has a store of calibration error information which can be used automatically to weight the signals derived from respective detecting means.

The "Perspex" wall 5 of the arrangement 2 need not be of the shape shown in FIG. 1. For example the walls through which the beam 3 passes need not be arcuate; they may be planar or shaped to provide a constant attenuation to radiation throughout the arrangement 2 when the body 1 is replaced by water. Moreover, the material used to construct these walls need not be "Perspex" for example PVC or other suitable plastics materials could be used.

In the apparatus described with reference to FIG. 1, the discharge rate of the integrators 10 is arranged to be linear, and for this reason the binary numbers fed into the store 12 from the counter 16 have to be converted into logarithmic values in order that the overall absorption suffered by radiation traversing the body along a path can be expressed as the sum of the absorptions of the elements of the matrix which are disposed along said path.

An alternative arrangement is to cause the integrators to discharge in accordance with a logarithmic law. When the charge held in an integrator has decayed to a threshold level, the corresponding bistable circuit 11 is arranged to feed a pulse via OR gate 11a to the AND gates 17. The operation from this point is the same as that described with reference to FIG. 1 except, of course, that the logarithmic conversion has already taken place so that it is unnecessary for the members fed into store 12 from the counter 16 to be so converted.

The threshold level referred to in the last preceding paragraph can be selected to suit individual applications and if a human torso is being examined, the threshold may be made such that an absorption level giving rise to a charge, in an integrator, which decays to the threshold level in a given time $t'$ is allocated a value of zero. Correspondingly, absorption levels giving rise to changes which decay to the threshold level in times less than $t'$ are designated positive (since greater absorption has occurred) whereas absorption levels giving rise to changes which decay to the threshold level in times greater than $t'$ are designated negative.

It will be appreciated that in practice it is convenient for a patient to lie supine with the required part of his torso inside the tubular, flexible wall 6. This can be achieved by arranging the apparatus with its axis of rotation horizontal and by placing suitable couches or the like on either side of the apparatus, the couches being adapted to support, respectively, the upper part and the lower part of the patient's body.

In a modification of the invention which is shown in part in FIG. 5, the rotary water seal used in the apparatus shown in FIG. 1 is dispensed with since the water enclosure is designed to remain stationary while the source and detectors orbit around it. In the apparatus shown in plan and part cross-sectional view in FIG. 5, a cylindrical outer wall 29 of "Perspex" (Registered Trade Mark) or other suitable material is formed with annular end flanges (not shown). Extending between the inner peripheries of the two annular flanges is a tubular, flexible inner wall 30 formed, for example, of rubber. The X-ray source and detectors (not shown) are mounted on a turntable member 31 which is annular and rotates around the cylindrical wall 29; the axis of rotation of the turntable being coincident with the longitudinal axis of the cylindrical wall 29. The operation of the apparatus is identical to that of FIG. 1 but since the water enclosure does not rotate, the need for the rotating water seal is avoided. Also, it is possible to provide a permanent connection between a water pump such as 24 (FIG. 1) and a water reservoir, avoiding the need for a valve such as 25a and a removeable pipe such as 25b (FIG. 1).

Although in the foregoing description reference has been made to the use of water to surround the part of the body being examined, it is stressed that the invention is not limited to the use of water. Other liquid media may be used and, in particular if the body being examined is not a human body, other liquids of different densities might be preferable to water. In general it is desirable to choose the liquid medium such that its absorption to the radiation being used is similar to the average absorption of said radiation by the body being examined.

Referring to FIG. 6, a body to be examined is located in a short flexible hose 1', which forms one wall of a water reservoir 2', the hose being shown in section on the drawing. The hose 1', made of rubber, for example, is attached at each end to a rigid ring secured to the frame of the apparatus, one of these rings being denoted by the reference 3'. The hose 1' is of sufficient size to allow the body of a patient to be examined to be inserted through the hose, so that the hose surrounds the abdomen for example. The other walls the reservoir 2', namely the end walls, one of which is shown at 4', and the outer wall 5', shown in section, are secured to a turntable 6', and to ensure that the reservoir is watertight, watertight seals, one of which is denoted at 7', are provided between the end rings 3' of the hose and the end walls 4' of the reservoir. After the body has been located within the hose 1', water is pumped into the reservoir by inlet 8', until the hose fits snugly around the patient, extruding air from between the patient and the hose. The walls 4' and 5' of the reservoir 2' are constructed of a plastics material which is substantially transparent to the radiation which is to be used in examining the body.

A source 9' of penetrating radiation such as X- or Y-radiation is arranged to produce a substantially planar sectoral swath 10' of the radiation and is mounted on the turntable 6'. It will be observed that the path lengths for all rays on the swath 10' through the reservoir are substantially equal though part of the paths for some rays will be through the body, not through the water. The source 9' can be orbited around the body in the plane of the swath by rotation of the turntable 6', which can be effected by means of an electrical motor 11' which drives a gear wheel 12' engaging with gear teeth (not shown) provided all around the inner periphery of a stationary member 13'. This member 13' is part of the frame of the apparatus to which the rings 3' are attached. As the outer wall 5' of the reservoir 2' is attached to the turntable, it rotates with it, and always presents the same profile to the swath 10'.

A bank of radiation sensitive crystals $14_1'$, $14_2'$ ... $14_r'$, are mounted on the turntable 6', so as to be generally disposed, as shown, on the opposite side of the body to the source 9'. Each crystal 14' can receive radiation via a respective collimator $15_1'$, $15_2'$ ... $15_r'$ which collimates the radiation into a beam through the body. Two such beams are denoted by the reference $16_n'$, $16_{n'+1}$. In this example, the crystals 14' each comprise a scintillator crystal which gives light pulses in response to incident radiation photons. Such light pulses are conveyed from each crystal via a respective light pipe $17_1'$, $17_2'$ ... $17_r'$ to a respective photo-multiplier $18_1'$, $18_2'$, ... $18_r'$. The photomultipliers 18' produce output electrical signals dependent upon the incident light from the respective crystals and these electrical input signals are applied via conductors $19_1'$, $19_2'$... $19_r'$ to a signal processing circuit 20'.

In operation, the output of each photo-multiplier is integrated for successive short intervals of time, during each of which the turntable 6' moves through only a small angle. There is thus produced for each of a series of small increments of the orbital motion of the turntable, a set of output signals from the photo-multipliers dependent on the absorption of the respective beams 16 in the body enclosed by the hose 1'. The timing of the integrations is controlled by a timing circuit 21' which controls the rate of rotation of the motor 11'. The processing circuit 20' is arranged to reconstruct an image of the variable absorption of the elements of the section of the body, which is traversed by the swath 10' of radiation. The circuit 20' may include a digital computer arranged to carry out image reconstruction in the manner described in the aforesaid Patent Specification No. 1,283,915, or in the manner described in the complete specification of our co-pending British patent application No. 19,528/73. To aid in the image reconstruction, the circuit 20' may include means for sorting the output signals, which are derived in sets corresponding to the beams defined by the collimators 15', into sets corresponding to parallel beams.

In the drawing, only a small number of detectors comprising crystals 14', optical couplings 17' and photomultipliers 18' are shown and it will be appreciated that many more such detectors will be provided in a practical apparatus. For example a hundred or more detectors may be used. The drawing, however, indicates in exaggerated fashion how, by reason of the physical size of the collimators the beams 16' are separated from each other by gaps which although traversed by the radiation do not contribute to the output signals. This leads to a reduction in the number of output signals which, for a given beam width can be used in the image reconstruction, and it therefore impairs the quality of the image reconstruction. For example, the shaded region 22' between the beams $16_n'$ and $16_{n'+1}$ makes no contribution to the output signals of the set which is derived when the turntable 6' is in the angular position shown in the drawings. There is of course a similar gap between each two adjacent beams 16'. However, as will be described, the apparatus illustrated enables information to be derived from the regions such as 22' so that the effective number of readings taken through the planar slice of the body can be substantially increased whilst using the same number of detectors.

As shown on the drawings the bank of collimators 15' and crystals 14' is made slidably movable in a pair of runners 23' which are fixedly mounted on the turntable 6' and the bank can be moved linearly in the direction shown by the arrow 24' by a distance corresponding to approximately one half of the spacing of the entrance apertures of the collimators.

This linear movement can be effected in a variety of ways, but is represented as being produced by a crank 24' connected to the bank of collimator 15' by a connecting link 25', the crank being driven by a motor 26', the operation of which is timed in relation to that of the motor 11' by the control circuit 21'. The photo-multipliers 18' do not take part in the "side-step" of the collimators 15' and crystals 14', and the light pipes 17' which optically couple the crystals 14' to the respective photo-multipliers 18' are sufficiently flexible to allow the side-step to occur. The linear motion of the collimator and the crystals is correlated with the rate of rotation of the turntable 6' such that the afore-mentioned distance of travel of the bank of detectors is achieved after 360' of rotation of the turntable 6'. The full amount of linear motion of the bank 11' of detectors is achieved in one step, i.e. the member 6' rotates through 360° with the bank collimators and crystals in the position shown in the drawing and then the bank is moved linearly through a distance corresponding to one half of the collimator spacing. The turntable member 6' then rotates through a further 360° with the bank in its new position. Thereafter the banks of collimators and crystals are returned to the first mentioned position, in readiness for the start of another examination. FIG. 7 shows an instructional four-step flow diagram by means of which the above sequence of operations may be carried out.

It will be appreciated that during the second of the two rotations, the relative positions of the beams 16' and the gap 22' are interchanged, compared with the first rotation.

During the second rotation, the output signals in the sets for corresponding angular positions are dependent upon absorption occurring in the areas which were missed by the output signals derived during the first rotation. The additional signals improve the quality of image reconstruction achieved by the circuit 20'. In general the beams 16' may be wider than the gaps so that there will be some overlapping of the beams during the first and second revolutions of the turntable 6'.

The side step of the collimators 15' and crystals 14' may occur after a rotation of 180°, instead of 360°. Where the step occurs at 360°, the beams during the second 180° of a complete revolution will substantially register with, though being oppositely directed from those of the first 180° rotation. However, this may be preferred, since it enables the output signals derived from the pairs of oppositely directed, but substantially registering beams, to be combined.

If the bank 11' of detectors is to be moved linearly through the aforementioned distance after 360° of rotation of the turntable 6', then instead of imparting the complete linear motion to the bank in one step as described above, the bank can be moved linearly at a slow rate, synchronously with the rotation of member 6', and throughout the 360° of rotation thereof, so that the bank has achieved the required amount of linear motion (i.e. half the collimator spacing) at the completion of the 360° of rotation. The turntable 6' then completes a further 360° of rotation whilst the bank moves through a further distance corresponding to half the inter-detector spacing. This arrangement can be achieved by driving the crank 24' continuously from the motor 11' via a gear box which provides a large reduction in rotational speed. The same modification can of course be employed when the requirement amount of linear motion is completed in 180° of rotation of the turntable 6'. It has been discovered that, in the arrangement in which the linear motion of the bank of collimators 15' is slow but continuous throughout a full revolution of turntable 6', the slight continuous precession of the detectors relative to the source 9' is of little consequence with regard to the determination of the aforementioned absorption (or transmission) coefficients.

In some cases only the collimators 15' may take part in the additional displacement provided each crystal can receive the radiation from its respective collimator in its different positions. On the other hand the photo-multipliers and the crystals may both take part in the additional displacement. Other forms of detectors than that illustrated may also be used.

In a modification of the invention, the number of absorption readings derived per detector can be increased further by causing the bank of detectors to move linearly at a slower rate than that previously envisaged so that the bank of collimators and crystals moves through the aforementioned distance corresponding to half the inter-detector spacing in, say, four revolutions of the turntable 6'. This can result in obtaining, for each angular orientation of the swath, output signals corresponding to substantially overlapping beams, which has special advantages which need not be described here. In this case, moreover, it is preferable that an apertured shutter be provided between the source 9' and the body. The shutter is moved linearly in synchronism with the linear motion of the collimators and crystals and effectively divides the sectoral swath 10' of radiation into discrete beams such as 16', which move relative to the body as the bank of collimators and crystals move. This reduces the amount of radiation to which the body is exposed.

Other embodiments of the invention will be evident to those skilled in the art, and it is not intended that the scope of the invention be limited by the preceding specific description of one embodiment of the invention, and modification thereof.

What is claimed is:

1. A method of radiographically examining the body of a patient in order to produce an image of the variation of absorption coefficient, with respect to penetrating radiation, over a planar region disposed in said body, comprising the steps of:
   a. projecting radiation through the body, in the plane of said region, from a position external of the body; the radiation conforming to a fan-shaped spread of angle which substantially equals, or exceeds, the angle subtended at said position by said region,
   b. scanning said spread of radiation relative to the body so as to irradiate said region from a plurality of different positions; the scanning consisting of an angular movement about an axis substantially perpendicular to said region,
   c. detecting the radiation emergent from the body, in said plane, along each of a plurality of mutually divergent beam paths within said spread from each of said positions, and providing an output signal indicative of the radiation transmitted through the body along each of said beam paths, d. shifting the positions of said beam paths, within said spread, during the angular movement so that output signals, provided during one portion of said angular movement, relate to beam paths interleaved with beam paths in respect of which output signals are provided during another portion of the angular movement, the relationship between the scanning and the shifting being such that the region is irradiated from a plurality of said positions during each of said portions, and e. processing the output signals to produce said image.

* * * * *